(12) United States Patent
Yang et al.

(10) Patent No.: US 12,378,361 B1
(45) Date of Patent: Aug. 5, 2025

(54) SELF-SENSITIZING NEGATIVE POLYIMIDE PRECURSOR AND METHOD FOR PREPARING THE SAME, AND USE THEREOF

(71) Applicant: SHANDONG NORMAL UNIVERSITY, Jinan (CN)

(72) Inventors: Peng Yang, Jinan (CN); Haiping Yu, Jinan (CN); Yuting Zhu, Jinan (CN); Xu Wang, Jinan (CN)

(73) Assignee: SHANDONG NORMAL UNIVERSITY, Jinan (CN)

( * ) Notice: Subject to any disclaimer, the term of this patent is extended or adjusted under 35 U.S.C. 154(b) by 0 days.

(21) Appl. No.: 19/204,700

(22) Filed: May 12, 2025

(30) Foreign Application Priority Data

Oct. 9, 2024 (CN) .......................... 202411402630.1

(51) Int. Cl.
| | |
|---|---|
| C08G 73/12 | (2006.01) |
| C07C 51/363 | (2006.01) |
| C07C 67/14 | (2006.01) |
| C07C 209/36 | (2006.01) |
| C08G 73/10 | (2006.01) |

(52) U.S. Cl.
CPC .......... *C08G 73/126* (2013.01); *C07C 51/363* (2013.01); *C07C 67/14* (2013.01); *C07C 209/36* (2013.01); *C08G 73/121* (2013.01); *C08G 73/122* (2013.01); C08G 73/101 (2013.01); C08G 73/1042 (2013.01); C08G 73/1067 (2013.01)

(58) Field of Classification Search
None
See application file for complete search history.

(56) References Cited

FOREIGN PATENT DOCUMENTS

| | | | |
|---|---|---|---|
| CN | 101555318 A | 10/2009 | |
| CN | 104371102 A | 2/2015 | |
| CN | 114907567 A | 8/2022 | |
| CN | 116478098 A | 7/2023 | |
| CN | 118667162 A * | 9/2024 | ............ G03F 7/004 |

(Continued)

*Primary Examiner* — Richard A. Huhn
(74) *Attorney, Agent, or Firm* — IPRO, PLLC (57) ABSTRACT

A self-sensitizing negative polyimide precursor and a method for preparing the same, and use thereof. 4,4'-dinitro-1,1'-biphenyl-2,2'-dicarboxylic acid is used as a starting material and undergoes an acylation reaction with thionyl chloride to afford compound 1. Compound 1 subsequently undergoes an esterification reaction with 2-hydroxyethyl methacrylate to afford compound 2. The nitro groups of compound 2 are then reduced to amino groups; after purification, an intermediate of the self-sensitizing negative polyimide precursor is obtained. The intermediate is polymerized with 3,3',4,4'-benzophenone tetracarboxylic dianhydride to give a polyamic acid, namely the self-sensitizing negative polyimide precursor. Because the intermediate contains a benzophenone moiety, ultraviolet irradiation can generate free radicals, allowing the intermediate to act intrinsically as a photoinitiator. The dual photosensitive properties of the ketone carbonyl and double bond in the self-sensitizing negative polyimide precursor material provided by the present application can improve the exposure sensitivity of the resin.

11 Claims, 4 Drawing Sheets

(56) References Cited

FOREIGN PATENT DOCUMENTS

| | | | | |
|---|---|---|---|---|
| JP | H0812759 A | 1/1996 | | |
| JP | H1072413 A | 3/1998 | | |
| JP | 2002161136 A | 6/2002 | | |
| KR | 20220092379 A | * | 7/2022 | ........... C07C 271/20 |

* cited by examiner

SELF-SENSITIZING NEGATIVE POLYIMIDE PRECURSOR AND METHOD FOR PREPARING THE SAME, AND USE THEREOF

CROSS-REFERENCE TO RELATED APPLICATIONS

The present application claims priority to Chinese Patent Application No. 202411402630.1, filed with the China National Intellectual Property Administration on Oct. 9, 2024, entitled "SELF-SENSITIZING NEGATIVE POLYIMIDE PRECURSOR AND METHOD FOR PREPARING THE SAME, AND USE THEREOF," the entire contents of which are incorporated herein by reference in their entirety for all purposes.

TECHNICAL FIELD

The present application relates to the field of polymer materials technology, and more particularly to a self-sensitizing negative polyimide precursor and a method for preparing the same, and use thereof.

BACKGROUND

The disclosure of the background art section is intended solely to enhance the understanding of the general background of the present invention and should not necessarily be regarded as an admission or implied acknowledgment that the information constitutes prior art known to those skilled in the art.

Polyimide materials are highly performance-functional materials with excellent properties, especially high-temperature resistance, insulation properties, and dielectric properties. Consequently, they are widely applied in military and aerospace fields. As civilian products, polyimides are extensively used in microelectronics, with photosensitive polyimides (PSPI) serving as buffer layers, passivation layers, and α-particle barrier layers in integrated circuits. Photoresist polyimides, along with polyimide films and polyimide liquid crystal alignment agents, have become one of the three primary applications of polyimides.

Based on dissolution characteristics after exposure, polyimides are classified as negative polyimides and positive polyimides. When processed through photolithography, positive polyimides are exposed through a mask, wherein the exposed areas undergo photolysis reactions that increase their solubility in developer, resulting in dissolution in the developer and ultimately producing a pattern identical to the mask. Conversely, negative polyimides undergo photochemical reactions after exposure through a mask, which reduces solubility in the exposed areas, while unexposed areas dissolve in the developer, ultimately yielding a pattern inverse to the mask.

Negative polyimides are further categorized as ester-type, ionic-type, and self-sensitizing negative polyimides. Ester-type and ionic-type polyimides require photoinitiators to trigger photochemical reactions, whereas self-sensitizing polyimides can undergo crosslinking reactions through their inherent benzophenone structures without requiring initiators. Under high-temperature curing, no small-molecule byproducts are generated, effectively addressing the volume shrinkage issues of ester-type and ionic-type photosensitive polyimides, and avoiding performance degradation in thermal, mechanical, and electrical properties caused by photoinitiator residues. Currently, existing negative self-sensitizing polyimides operate via two photochemical reaction mechanisms: one involves crosslinking between benzophenone and methyl groups adjacent to amino groups, requiring diamine monomers with two methyl groups adjacent to the amino position, which are difficult to synthesize and expensive, and exhibit poor photosensitivity; the other involves benzophenone-initiated crosslinking of methacrylic acid side chains, which offers good photosensitivity but requires dimethyl sulfoxide or methacryloyl chloride during synthesis, generating chloride ions and acidic hydrogen ions that degrade the electrical properties of the photoresist and corrode the substrate.

SUMMARY

To overcome the aforementioned problems, the present application provides a self-sensitizing negative polyimide precursor and a method for preparing the same, and use thereof.

To achieve this technical objective, the present application employs the following technical solutions:

in a first aspect, the present application provides an intermediate for a self-sensitizing negative polyimide precursor, having the structure represented by Formula (I):

Formula (I).

In a second aspect, the present application provides a method for preparing the intermediate for the self-sensitizing negative polyimide precursor described above, comprising:

(1) reacting 4,4'-dinitro-1,1'-biphenyl-2,2'-dicarboxylic acid with thionyl chloride to obtain compound 1;

(2) dissolving compound 1 in an organic solvent 1, adding 2-hydroxyethyl methacrylate, and reacting to obtain compound 2;

(3) dissolving compound 2 in an organic solvent 2, and reacting under catalysis to obtain the intermediate for the self-sensitizing negative polyimide precursor;

wherein compound 1 has the structure represented by Formula (II):

Formula (II);

compound 2 has the structure represented by Formula (III):

Formula (III).

In a third aspect, the present application provides a use of the intermediate for the self-sensitizing negative polyimide precursor described in the first aspect for synthesizing a self-sensitizing negative polyimide precursor.

In a fourth aspect, the present application provides a self-sensitizing negative polyimide precursor, wherein the self-sensitizing negative polyimide precursor is obtained by polymerizing the intermediate for the self-sensitizing negative polyimide precursor with 3,3',4,4'-benzophenone tetracarboxylic dianhydride; wherein a molar ratio of the intermediate for the self-sensitizing negative polyimide precursor to 3,3',4,4'-benzophenone tetracarboxylic dianhydride is 0.8~1.2:1, the polymerizing is carried out by stirring at room temperature, and a reaction time of 18~26 h is employed.

In a fifth aspect, the present application provides a method for preparing a self-sensitizing negative polyimide precursor, comprising stirring the intermediate for the self-sensitizing negative polyimide precursor with 3,3',4,4'-benzophenone tetracarboxylic dianhydride at room temperature to obtain the self-sensitizing negative polyimide precursor;
wherein a molar ratio of the intermediate for the self-sensitizing negative polyimide precursor to 3,3',4,4'-benzophenone tetracarboxylic dianhydride is 0.8~1.2:1; a reaction time of 18~26 h under stirring at room temperature is employed.

In a sixth aspect, the present application provides a use of the self-sensitizing negative polyimide precursor described above in preparing a negative photoresist.

The beneficial effects of the present invention are as follows:

(1) In the present invention, 4,4'-dinitro-1,1'-biphenyl-2,2'-dicarboxylic acid is used as the starting material and reacts with thionyl chloride in an acylation reaction to obtain compound 1; compound 1 is not isolated and undergoes an esterification reaction with 2-hydroxyethyl methacrylate under pyridine catalysis to obtain compound 2; then using iron and hydrochloric acid as catalysts, the nitro group of compound 2 is reduced to an amino group, and after purification, the intermediate for the self-sensitizing negative polyimide precursor is obtained. The intermediate for the self-sensitizing negative polyimide precursor polymerizes with 3,3',4,4'-benzophenone tetracarboxylic dianhydride to obtain polyamic acid, namely the self-sensitizing negative polyimide precursor. In the present application, a cross-linking group (methacrylate) is pre-introduced into the intermediate for the self-sensitizing negative polyimide precursor, making the polymer synthesis process shorter and greener, requiring only the polymerization of two monomers in a solvent to form the self-sensitizing negative polyimide precursor, with no need for purification, and the reaction solution can be directly used for photolithography.

(2) The intermediate for the self-sensitizing negative polyimide precursor in the present invention contains a benzophenone structure, which can generate free radicals under ultraviolet light irradiation, thereby achieving a photoinitiator effect. The dual photosensitive properties of the ketone carbonyl and double bond in the self-sensitizing negative polyimide precursor material provided by the present application can improve the exposure sensitivity of the resin. Additionally, the present application first synthesizes the self-sensitizing negative polyimide precursor material at low temperature, utilizing the benzophenone structure in the main chain and the methacrylate in the side chain for cross-linking at low temperature, avoiding problems such as wafer warping that occur during high-temperature imidization.

(3) When the self-sensitizing negative polyimide precursor prepared by the present application is used as a photoresist, an alkaline solution can be used for development, avoiding environmental pollution problems caused by organic solvents.

BRIEF DESCRIPTION OF THE DRAWINGS

The accompanying drawings to the specification, which form part of the the present invention, are used to provide a further understanding of the present invention, and the illustrative examples of the present invention and the description thereof are used to explain the present invention and are not unduly limiting the present invention.

DESCRIPTION OF THE PREFERRED EMBODIMENTS

It should be noted that the following detailed descriptions are all illustrative and intended to provide further clarification of the present invention. Unless otherwise specified, all technical and scientific terms used in the present invention have the same meaning as commonly understood by those of ordinary skill in the art to which the present invention belongs.

It should be noted that the terminology used here is for the purpose of describing particular embodiments only and is not intended to be limiting of the exemplary embodiments of the invention. As used herein, the singular form is intended to include the plural form as well, unless the context clearly indicates otherwise, and it should also be understood that when the terms "comprising" and/or "including" are used in this specification, they indicate the presence of features, steps, operations, devices, components, and/or combinations thereof.

In a first typical embodiment, the present application provides an intermediate for a self-sensitizing negative polyimide precursor, having the structure represented by Formula (I):

Formula (I).

In a second typical embodiment, the present application provides a method for preparing the intermediate for the self-sensitizing negative polyimide precursor described above, comprising:

(1) reacting 4,4'-dinitro-1,1'-biphenyl-2,2'-dicarboxylic acid with thionyl chloride to obtain compound 1;
(2) dissolving compound 1 in an organic solvent 1, adding 2-hydroxyethyl methacrylate, and reacting to obtain compound 2;
(3) dissolving compound 2 in an organic solvent 2, and reacting under catalysis to obtain the intermediate for the self-sensitizing negative polyimide precursor;

wherein compound 1 has the structure represented by Formula (II):

Formula (II);

compound 2 has the structure represented by Formula (III):

Formula (III).

In one or more embodiments, step (1) is carried out under an inert gas atmosphere.

In one or more embodiments, in step (1), a molar ratio of 4,4'-dinitro-1,1'-biphenyl-2,2'-dicarboxylic acid to thionyl chloride is 1:(95~133), preferably 1:133.

In one or more embodiments, in step (1), a reaction temperature of 75~90° C. is employed, preferably 80° C.; a reaction time of 1.5~3 h is employed, preferably 2 h.

In one or more embodiments, step (2) comprises: dissolving compound 1 in an organic solvent 1, adding 2-hydroxyethyl methacrylate, and reacting under pyridine catalysis to obtain compound 2.

Preferably, the organic solvent 1 includes acetone.

Preferably, a molar ratio of compound 1 to 2-hydroxyethyl methacrylate is 1:(2~3), preferably 1:2.

Preferably, a molar ratio of compound 1 to pyridine is 1:(1~2), preferably 1:1.

Preferably, a reaction temperature of 95~105° C. is employed, more preferably 100° C.; and a reaction time of 2~5 h is employed.

In one or more embodiments, step (3) comprises: dissolving compound 2 in an organic solvent 2, and reacting under the catalysis of iron powder and hydrochloric acid to obtain the intermediate for the self-sensitizing negative polyimide precursor.

Preferably, the organic solvent 2 includes a mixed solution of isopropanol and water, wherein a volume ratio of isopropanol to water is 3.5~5:1, preferably 4:1.

Preferably, a molar ratio of compound 2 to iron powder is 1:8~12, preferably 1:10.

Preferably, a molar ratio of compound 2 to hydrochloric acid is 6~10:1, preferably 8.3:1.

Preferably, a reaction temperature of 95~105° C. is employed, more preferably 100° C.; and a reaction time of 1~3 h is employed.

In a third typical embodiment, the present application provides a use of the intermediate for the self-sensitizing negative polyimide precursor described in the first aspect for synthesizing a self-sensitizing negative polyimide precursor.

In a fourth typical embodiment, the present application provides a self-sensitizing negative polyimide precursor, wherein the self-sensitizing negative polyimide precursor is obtained by polymerizing the intermediate for the self-sensitizing negative polyimide precursor with 3,3',4,4'-benzophenone tetracarboxylic dianhydride; wherein a molar ratio of the intermediate for the self-sensitizing negative polyimide precursor to 3,3',4,4'-benzophenone tetracarboxylic dianhydride is 0.8~1.2:1, the polymerizing is carried out by stirring at room temperature, and a reaction time of 18~26 h is employed.

In one or more embodiments, the self-sensitizing negative polyimide precursor is obtained by polymerizing the intermediate for the self-sensitizing negative polyimide precursor with 3,3',4,4'-benzophenone tetracarboxylic dianhydride in an organic solvent under an inert gas atmosphere.

Preferably, the organic solvent includes N-methyl-2-pyrrolidone.

In one or more embodiments, a molar ratio of the intermediate for the self-sensitizing negative polyimide precursor to 3,3',4,4'-benzophenone tetracarboxylic dianhydride is 1:1.

In one or more embodiments, the reaction time is 20 h.

In a fifth typical embodiment, the present application provides a method for preparing a self-sensitizing negative polyimide precursor, comprising stirring the intermediate for the self-sensitizing negative polyimide precursor with 3,3',4,4'-benzophenone tetracarboxylic dianhydride at room temperature to obtain the self-sensitizing negative polyimide precursor;

wherein a molar ratio of the intermediate for the self-sensitizing negative polyimide precursor to 3,3',4,4'-benzophenone tetracarboxylic dianhydride is 0.8~1.2:1;

wherein a reaction time of 18~26 h under stirring at room temperature is employed.

In one or more embodiments, the self-sensitizing negative polyimide precursor is obtained by stirring the intermediate for the self-sensitizing negative polyimide precursor with 3,3',4,4'-benzophenone tetracarboxylic dianhydride in an organic solvent under an inert gas atmosphere.

Preferably, the organic solvent includes N-methyl-2-pyrrolidone.

In one or more embodiments, a molar ratio of the intermediate for the self-sensitizing negative polyimide precursor to 3,3',4,4'-benzophenone tetracarboxylic dianhydride is 1:1.

In one or more embodiments, the polymerizing step is carried out for 20 h.

In a sixth aspect, the present application provides a use of the self-sensitizing negative polyimide precursor described above in preparing a negative photoresist.

To enable persons of ordinary skill in the art to more clearly understand the technical solutions of the present application, the technical solutions of the present application will be described in detail in conjunction with specific examples.

The chemical raw materials used in the examples of the present application are commercially available products.

Figure 1:
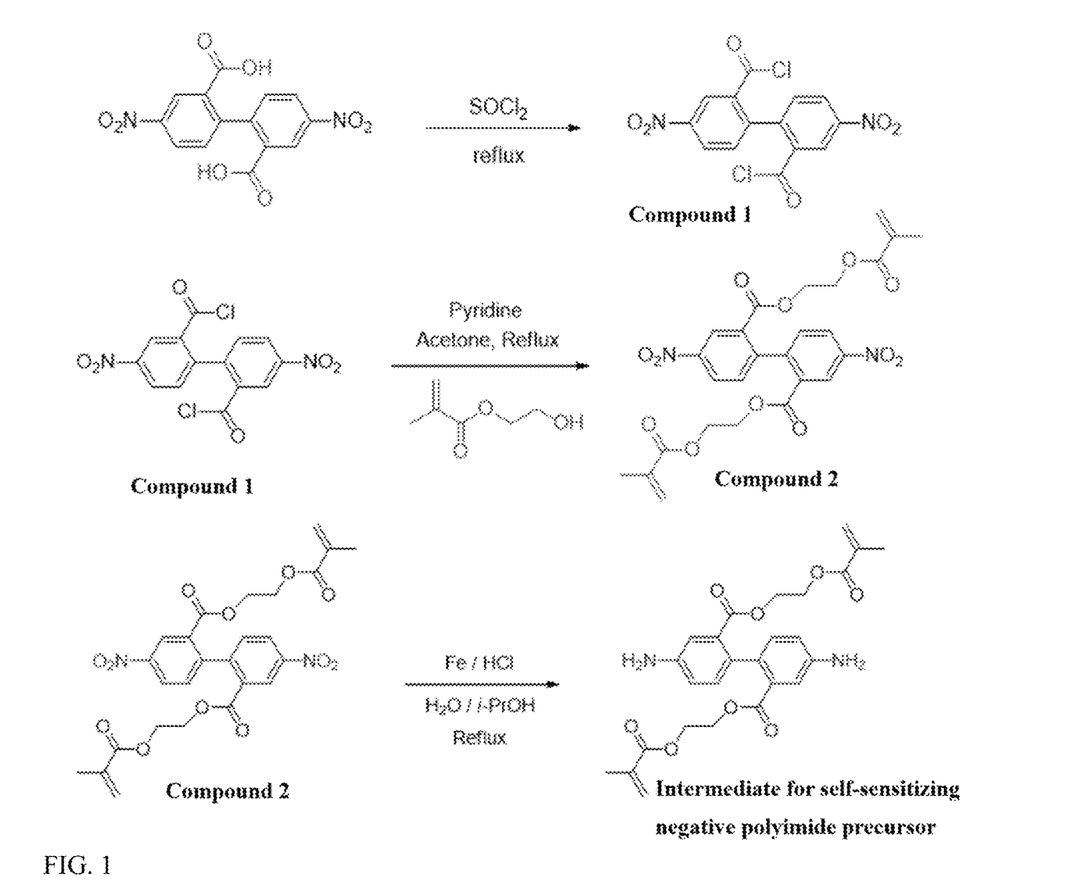
FIG. 1 shows the synthesis route of the intermediate for the self-sensitizing negative polyimide precursor in the present application.

FIG. 1 shows the synthesis route of the intermediate for the self-sensitizing negative polyimide precursor in the present application. Referring to FIG. 1, the self-sensitizing negative polyimide precursor is synthesized.

Example 1

4,4'-dinitro-1,1'-biphenyl-2,2'-dicarboxylic acid (5.0 g, 15 mmol) was added to excess thionyl chloride (150 mL), and the mixture was heated to reflux at 80° C. under nitrogen for 2 hours. After the reaction was complete, the mixture was cooled to room temperature, concentrated under reduced pressure, and used directly for the next step. The product compound 1 was a white solid with a yield of 95%.

NMR data is as follows: $^1$H NMR (400 MHZ, CDCl$_3$) δ 9.19 (d, J=2.2 Hz, 1H), 8.57 (dd, J=8.4, 2.2 Hz, 1H), 7.44 (d, J=8.4 Hz, 1H).

$^{13}$C NMR (100 MHz, CDCl$_3$) δ 166.30, 147.98, 145.94, 133.50, 131.12, 128.61, 128.20.

Example 2

At 0° C., compound 1 (5.5 g, 15 mmol), acetone (7.2 mL), and pyridine (1.2 mL, 15 mmol) were sequentially added to a reaction flask, followed by slow dropwise addition of 2-hydroxyethyl methacrylate (3.7 mL, 30 mmol). The reaction mixture was refluxed at 100° C. for 2 hours. Upon completion of the reaction, the reaction mixture was cooled to room temperature, and water was added to quench the reaction. The reaction mixture was extracted three times with dichloromethane, dried over anhydrous sodium sulfate, and the solvent was removed using a rotary evaporator. The residue was purified by silica gel column chromatography using petroleum ether/ethyl acetate (5:1) as the eluent. Compound 2 was a pale yellow viscous liquid with a yield of 80%.

NMR data is as follows:

$^1$H NMR (400 MHZ, CDCl$_3$) δ 8.92 (d, J=2.3 Hz, 2H), 8.43 (dd, J=8.4, 2.3 Hz, 2H), 7.40 (d, J=8.4 Hz, 2H), 6.08 (s, 2H), 5.61 (s, 2H), 4.41-4.38 (m, 4H), 4.28-4.26 (m, 4H), 1.93 (s, 6H).

$^{13}$C NMR (100 MHZ, CDCl$_3$) δ 166.81, 163.85, 147.66, 147.41, 135.69, 130.78, 129.86, 126.45, 126.25, 125.49, 63.50, 61.86, 18.13.

HRMS (ESI): calculated for $C_{26}H_{24}N_2O_{12}$ [M+Na]$^+$: 579.1227, found: 579.1226.

Example 3

Compound 2 (3.9 g, 7 mmol), iron powder (3.9 g, 70 mmol, 100 mesh), concentrated hydrochloric acid (commercially available hydrochloric acid with a mass fraction of 37%, 70 μL), isopropanol (11.2 mL) and single-distilled water (2.8 mL) were sequentially added to a reaction flask. After refluxing at 100° C. for 15 minutes, additional iron powder (3.9 g, 70 mmol, 100 mesh) and hydrochloric acid (70 μL) were added to the reaction flask, and refluxing was continued at 100° C. for 1 hour. Upon completion of the reaction, the reaction mixture was cooled to room temperature, filtered to remove excess iron powder, and washed with dichloromethane. The filtrate was extracted three times with dichloromethane, dried over anhydrous sodium sulfate, and the solvent was removed using a rotary evaporator. The residue was purified by silica gel column chromatography using petroleum ether/ethyl acetate (1:1) as the eluent. The intermediate for the self-sensitizing negative polyimide precursor was a yellow viscous liquid with a yield of 76%.

NMR data is as follows:

$^1$H NMR (400 MHZ, CDCl$_3$) δ 7.25 (d, J=2.3 Hz, 2H), 6.95 (d, J=8.1 Hz, 2H), 6.77 (dd, J=8.1, 2.4 Hz, 2H), 6.07 (s, 2H), 5.57 (s, 2H), 4.26-4.22 (m, 4H), 4.07-4.03 (m, 4H), 3.78 (s, 4H), 1.92 (s, 6H).

$^{13}$C NMR (100 MHZ, CDCl$_3$) δ 167.13, 166.96, 145.24, 135.91, 133.28, 131.63, 130.15, 125.89, 118.05, 116.07, 62.35, 62.05, 18.20.

HRMS (ESI): calculated for $C_{26}H_{28}N_2O_8$ [M+Na]$^+$: 519.1744, found: 519.1741.

Figure 2:
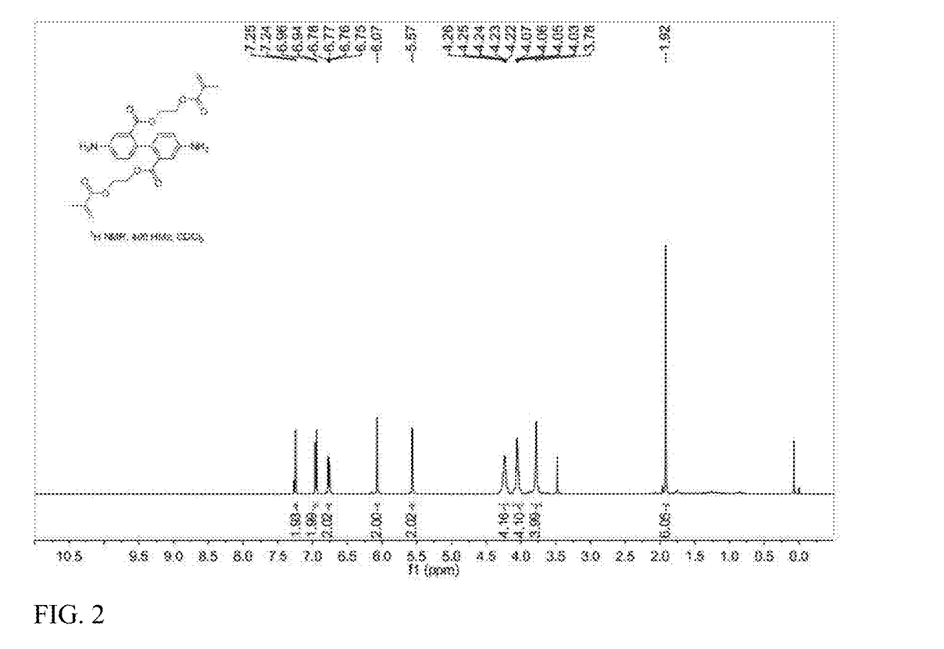
FIG. 2 shows the 1H NMR spectrum of the intermediate for the self-sensitizing negative polyimide precursor.

FIG. 2 illustrates the $^1$H NMR spectrum of the intermediate for the self-sensitizing negative polyimide precursor.

Figure 4:
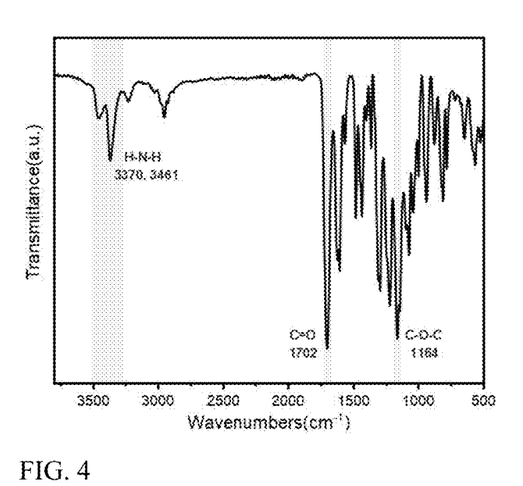
FIG. 4 shows the infrared spectrum of the intermediate for the self-sensitizing negative polyimide precursor.

FIG. 4 illustrates the infrared (IR) spectrum of the intermediate for the self-sensitizing negative polyimide precursor.

Example 4

Under nitrogen, the intermediate for the self-sensitizing negative polyimide precursor (3.0 g, 6 mmol) and super-dry N-methyl-2-pyrrolidone (20 mL) were sequentially added to a reaction flask, and the reaction mixture was stirred at 10~15° C. for 30 minutes to obtain a transparent solution. Then 3,3',4,4'-benzophenone tetracarboxylic dianhydride (2.0 g, 6 mmol) together with additional super-dry N-methyl-2-pyrrolidone (7.6 mL) were added to the reaction solution, resulting in a reaction mixture with a solid content of 15 wt %. The reaction temperature was raised to room temperature, and the polymerization system was stirred at room temperature for 20 hours to obtain a high-viscosity solution, which was the self-sensitizing negative polyimide precursor (polyamic acid). Acetic anhydride (2.8 mL, 30 mmol) and pyridine (1.9 mL, 24 mmol), both dried over molecular sieves, were added to the solution, followed by super-dry N-methyl-2-pyrrolidone (60 mL), and the system was heated to 50° C. and stirred for 24 hours to obtain a polyimide solution. The homogeneous polyimide solution was poured into an ethanol aqueous solution (150 mL, 75 vol %) and filtered to obtain a pale yellow solid, which was washed three times with methanol and transferred to a vacuum drying oven, dried overnight at 50° C. to obtain a pale yellow solid polyimide. The NMR datas of the polyamic acid and polyimide are as follows:

Self-Sensitizing Negative Polyimide Precursor (Polyamic Acid):

$^1$H NMR (400 MHZ, DMSO) δ 13.56 (s, 2H), 10.84 (s, 2H), 8.36-8.32 (m, 3H), 8.17-8.04 (m, 2H), 8.07-8.00 (m, 2H), 7.94-7.90 (m, 3H), 7.25 (s, 2H), 6.04 (s, 2H), 5.72 (s, 2H), 4.31 (s, 4H), 4.15 (s, 4H), 1.89 (s, 6H).

Self-Sensitizing Negative Polyimide:

$^1$H NMR (400 MHZ, DMSO) δ 8.42-8.02 (m, 4H), 7.79 (d, J=8.2 Hz, 1H), 7.50 (d, J=7.6 Hz, 1H), 5.96 (s, 1H), 5.64 (s, 1H), 4.28 (s, 2H), 4.13 (s, 2H), 1.81 (s, 3H).

Figure 3:
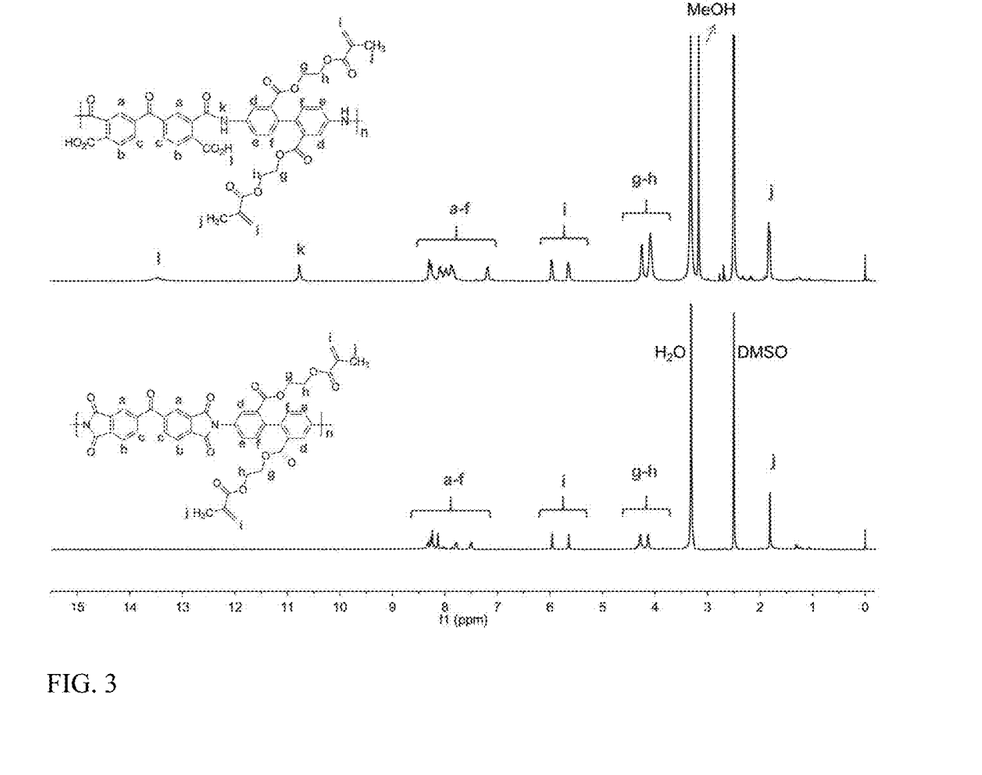
FIG. 3 shows the 1H NMR spectrum of the self-sensitizing negative polyimide precursor and the self-sensitizing negative polyimide, and signal assignments.

FIG. 3 shows the $^1$H NMR spectrum of the self-sensitizing negative polyimide precursor and the self-sensitizing negative polyimide, and signal assignments.

From FIG. 3, it can be seen that the common parts of the polyimide and the precursor include: multiple peaks at 7.2~8.5 ppm for hydrogen on the benzene rings of the polymer, two groups of peaks at 5.6~6.0 ppm for hydrogen on the alkene in the side chain, two groups of peaks at 4.1~4.3 ppm for hydrogen on the two methylene groups in the side chain, and peaks at 1.8 ppm for hydrogen on the methyl group in the side chain. The different parts between the polyimide and the precursor include: two signals in the precursor, peaks at 13.5 ppm for hydrogen on the carboxyl group of the precursor, and peaks at 10.8 ppm for hydrogen on the amide, which disappear after cyclization to form the polyimide. Additionally, the polyimide has a symmetrical structure, with the integral in the $^1$H NMR spectrum being half.

The above NMR analysis confirms the successful synthesis of the polyimide and the precursor.

Figure 5:
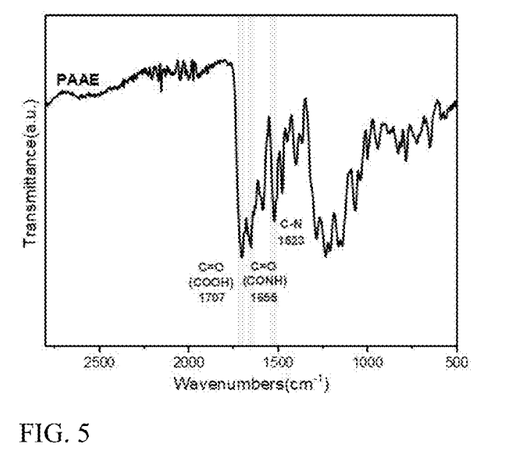
FIG. 5 shows the infrared spectrum of the self-sensitizing negative polyimide precursor (polyamic acid).
Figure 6:
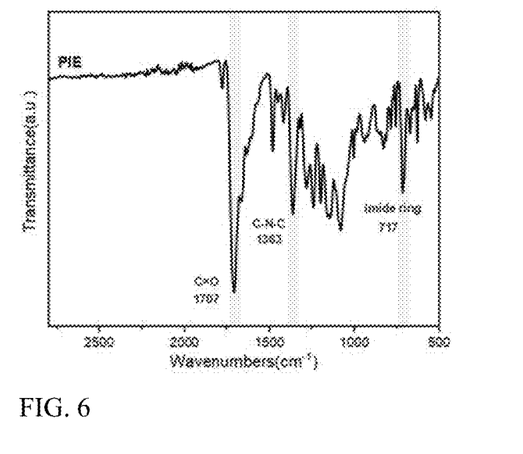
FIG. 6 shows the infrared spectrum of the polyimide synthesized by cyclization of the self-sensitizing negative polyimide precursor.

FIG. 5 shows the infrared spectrum of the self-sensitizing negative polyimide precursor. FIG. 6 shows the infrared spectrum of the polyimide synthesized by cyclization of the self-sensitizing negative polyimide precursor.

The molecular structure of the self-sensitizing negative polyimide precursor is shown in Formula (IV):

Formula (IV)

The final polyimide molecular structure is shown in Formula (V):

Formula (V)

Since the self-sensitizing negative polyimide precursor molecule shown in Formula (IV) contains too many carboxyl groups, its molecular weight cannot be directly measured. After further cyclization to synthesize the polyimide molecule shown in Formula (V), the molecular weight Mn of the polyimide molecule was determined to be 4395 Daltons, with a dispersion coefficient Mw/Mn of 1.67.

Experimental Example 1

Performance testing of the self-sensitizing negative polyimide precursor.

Figure 7:
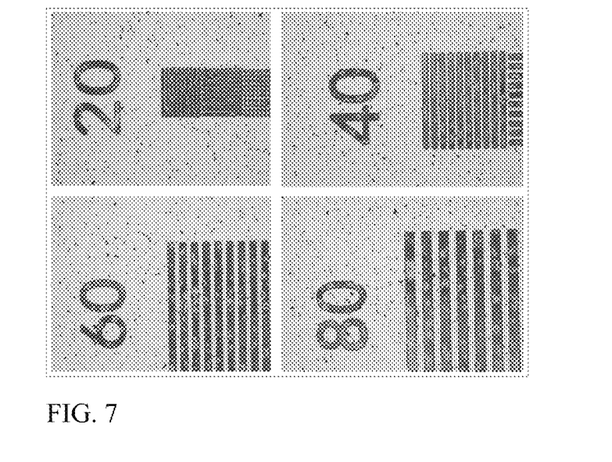
FIG. 7 shows a metallographic microscope photograph after photolithography and development of the self-sensitizing negative polyimide precursor.
Figure 8:
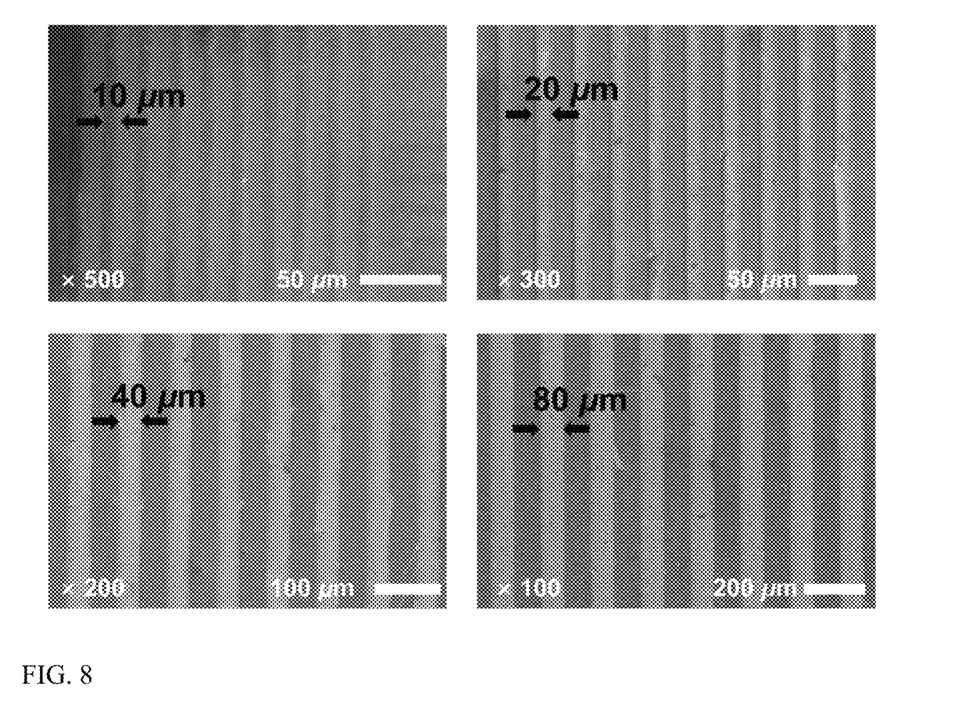
FIG. 8 shows scanning electron microscope images after photolithography and development of the self-sensitizing negative polyimide precursor, showing morphologies of line widths of 10 μm, 20 μm, 40 μm, and 80 μm, respectively.

The self-sensitizing negative polyimide precursor was dissolved in N-methyl-2-pyrrolidone, with a mass fraction of 10% in the mixed solution. The mixture was ultrasonicated for 1 hour to ensure complete dissolution, and then filtered using a 0.45 micron filter membrane to remove insoluble matter, resulting in a homogeneous solution. The obtained solution was coated onto a 4-inch silicon wafer using a spin-coating method at a rotation speed of 1000 r for 20 s, then dried at 100° C. for 3 min, resulting in a pre-baked film with a thickness of 0.68 μm on the silicon wafer. Next, using the i-line (365 nm) of a mercury lamp, the film was exposed through a mask, then developed using a $Na_2CO_3$ developer (mass fraction of 1%) to remove the exposed parts, resulting in a pre-baked resin film with specific patterns. A metallographic microscope image of the film after photolithography and development is shown in FIG. 7. Scanning electron microscope (SEM) images of the self-sensitizing negative polyimide precursor after photolithography and development are presented in FIG. 8. A photomask containing slits of varying line widths was used for lithographic testing. The SEM observations revealed well-defined patterns with line widths of 10 μm, 20 μm, 40 μm, and 80 μm, respectively. Even at a minimum line width of 10 μm, the pattern fidelity remained excellent, indicating a photoresist resolution of 10 μm.

The above descriptions are merely preferred embodiments of the present invention and are not intended to limit the present invention. For those skilled in the art, various changes and modifications can be made to the present invention. Any modification, equivalent replacement, or improvement made within the spirit and principles of the present invention should be included within the scope of the present invention's protection.

The invention claimed is:

1. An intermediate for a self-sensitizing negative polyimide precursor, having the structure represented by Formula (I):

Formula (I)

2. A method of preparing the intermediate for the self-sensitizing negative polyimide precursor of claim 1, comprising:

(1) reacting 4,4'-dinitro-1,1'-biphenyl-2,2'-dicarboxylic acid with thionyl chloride to obtain compound 1;

(2) dissolving compound 1 in an organic solvent 1, adding 2-hydroxyethyl methacrylate, and reacting to obtain compound 2;

(3) dissolving compound 2 in an organic solvent 2, and reacting under catalysis of iron powder and hydrochloric acid to obtain the intermediate for the self-sensitizing negative polyimide precursor;

wherein compound 1 has the structure represented by Formula (II):

Formula (II)

compound 2 has the structure represented by Formula (III):

Formula (III)

3. The method of claim 2, wherein step (1) is carried out under an inert gas atmosphere; or in step (1), a molar ratio of 4,4'-dinitro-1,1'-biphenyl-2,2'-dicarboxylic acid to thionyl chloride is 1:(95-133); or in step (1), a reaction temperature of 75~90° C. and a reaction time of 1.5~3 h are employed.

4. The method of claim 3, wherein in step (1), the molar ratio of 4,4'-dinitro-1,1'-biphenyl-2,2'-dicarboxylic acid to thionyl chloride is 1:133;

in step (1), the reaction temperature is 80° C., and the reaction time is 2 h.

5. The method of claim 2, wherein step (2) comprises: dissolving compound 1 in the organic solvent 1, adding 2-hydroxyethyl methacrylate, and reacting under pyridine catalysis to obtain compound 2;

the organic solvent 1 comprises acetone;

a molar ratio of compound 1 to 2-hydroxyethyl methacrylate is 1:(2~3);

a molar ratio of compound 1 to pyridine is 1:(1~2);

a reaction temperature of 95~105° C. and a reaction time of 2~5 h are employed.

6. The method of claim 5, wherein the molar ratio of compound 1 to 2-hydroxyethyl methacrylate is 1:2;

the molar ratio of compound 1 to pyridine is 1:1, and the reaction temperature is 100° C.

7. The method of claim 2, wherein, in step (3), the organic solvent 2 comprises a mixed solution of isopropanol and water, and a volume ratio of isopropanol to water is (3.5~5):1;

a molar ratio of compound 2 to iron powder is 1:(8~12);

a molar ratio of compound 2 to hydrochloric acid is (6~10):1;

a reaction temperature of 95~105° C. and a reaction time of 1~3 h are employed.

8. The method of claim 7, wherein the volume ratio of isopropanol to water is 4:1;

the molar ratio of compound 2 to iron powder is 1:10;

the molar ratio of compound 2 to hydrochloric acid is 8.3:1, and the reaction temperature is 100° C.

9. A self-sensitizing negative polyimide precursor, wherein the precursor is obtained by polymerizing the intermediate for the self-sensitizing negative polyimide precursor of claim 1 with 3,3',4,4'-benzophenone tetracarboxylic dianhydride, wherein a molar ratio of the intermediate for the self-sensitizing negative polyimide precursor to 3,3',4,4'-benzophenone tetracarboxylic dianhydride is 0.8~1.2:1, the polymerizing is carried out with stirring at room temperature, and a reaction time of 18~26 h is employed.

10. The self-sensitizing negative polyimide precursor of claim 9, wherein the self-sensitizing negative polyimide precursor is obtained by polymerizing the intermediate for the self-sensitizing negative polyimide precursor with 3,3',4,4'-benzophenone tetracarboxylic dianhydride in an organic solvent under an inert gas atmosphere;

wherein the organic solvent comprises N-methyl-2-pyrrolidone; or the molar ratio of the intermediate for the self-sensitizing negative polyimide precursor to 3,3',4,4'-benzophenone tetracarboxylic dianhydride is 1:1; or the reaction time is 20 h.

11. A method for preparing the self-sensitizing negative polyimide precursor of claim 9, comprising stirring an intermediate for the self-sensitizing negative polyimide precursor with 3,3',4,4'-benzophenone tetracarboxylic dianhydride to obtain the self-sensitizing negative polyimide precursor;

wherein a molar ratio of the intermediate for the self-sensitizing negative polyimide precursor to 3,3',4,4'-benzophenone tetracarboxylic dianhydride is 0.8~1.2:1; and a reaction time of 18~26 h under stirring at room temperature is employed;

wherein the intermediate for the self-sensitizing negative polyimide precursor has the structure represented by Formula (I):

Formula (I)

* * * * *